United States Patent [19]

Matsukawa et al.

[11] Patent Number: 4,970,323
[45] Date of Patent: Nov. 13, 1990

[54] PREPARATION PROCESS OF N-SUBSTITUTED MONOCHLOROSUCCINIMIDES

[75] Inventors: Mihaya Matsukawa; Masaru Wada; Hiroshi Suizu; Masayuki Furuya; Teruyuki Nagata, all of Omuta, Japan

[73] Assignee: Mitsu I Toatsu Chemicals, Inc., Tokyo, Japan

[21] Appl. No.: 370,211

[22] Filed: Jun. 22, 1989

[30] Foreign Application Priority Data

Jun. 30, 1988 [JP] Japan .................................. 63-163440

[51] Int. Cl.$^5$ ................. C07D 207/404; C07D 403/10
[52] U.S. Cl. ..................................... 548/545; 548/520
[58] Field of Search ................................ 548/545, 520

[56] References Cited

U.S. PATENT DOCUMENTS 3,465,002  9/1969  Bolhofer et al. .................... 548/545

OTHER PUBLICATIONS

Pyriadi, J. Org. Chem., vol. 37, No. 25, 1972, pp. 4184–4186.

*Primary Examiner*—David B. Springer
*Attorney, Agent, or Firm*—Millen, White & Zelano

[57] ABSTRACT

N-substituted monochlorosuccinimides e.g., N-phenyl-monochlorosuccinimide, can be prepared in a high yield by reacting a maleamic acid, e.g., N-phenylmaleamic acid, with phosgene in the presence of a catalyst, e.g., dimethylformamide.

17 Claims, No Drawings

PREPARATION PROCESS OF N-SUBSTITUTED MONOCHLOROSUCCINIMIDES

BACKGROUND OF THE INVENTION

The present invention relates to a process for the preparation of N-substituted monochlorosuccinimides.

N-Substituted monochlorosuccinimides are useful as intermediates for the production of resins, medicines and agricultural chemicals and also as precursors of N-substituted maleimides which have recently been utilized as a compound of optical elements.

The conventionally known process for preparing N-substituted monochlorosuccinimide is by ring closure and simultaneous hydrogen chloride addition reaction of a corresponding maleamic acid using an inorganic chlorine compound, such as phosphorus pentachloride and thionyl chloride, or an organic chlorine compound, such as acetyl chloride. For example, a process for preparing N-substituted monochloro-succinimide by reacting maleamic acid with phosphorus pentachloride or thionyl chloride in the absence of a solvent has been described in Journal of General Chemistry of USSR, 26, 211–225 (1956).

In addition, the results of an investigation of the reaction mechanism of maleamic acid with thionyl chloride or acetyl chloride under various reaction conditions have been reported in Journal of Organic Chemistry, 37, 4184–4186(1972).

These conventionally known processes do not provide the desired products in a high yield. Also thionyl chloride evolves toxic sulfur dioxide gas. Phosphorus pentachloride generates phosphorus oxychloride, which is difficult to separate or remove. Consequently, these processes are unsuitable for industrial application.

SUMMARY OF THE INVENTION

An object of this invention is to provide a industrial process for preparing N-substituted monochlorosuccinimide under mild conditions in a high yield.

The object of this invention was achieved by the discovery that an N-substituted monochlorosuccinimide can be readily prepared in an almost theoretical yield by reacting the corresponding maleamic acid in the presence of a catalyst with phosgene, which is produced on a large scale as a result of a recent development in the polyurethane industry and is available at a low price.

DETAILED DESCRIPTION OF THE INVENTION

N-substituted monochlorosuccinimides represented by the formula (II):

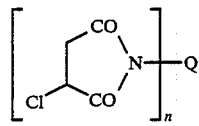
(II)

wherein n is the integer 1 or 2 and, when n is 1, Q is of an unsubstituted or substituted aryl group, an alkyl group or a cyclohexyl group and, when n is 2, Q is a divalent organic group of an unsubstituted or substituted phenylene group, an unsubstituted or substituted naphthylene group, or a p-bicyclic aryl group of the formula

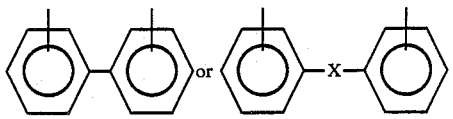

wherein X is a divalent bridging group of

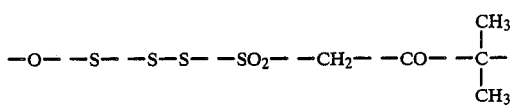

which comprises reacting a maleamic acid represented by the formula (I):

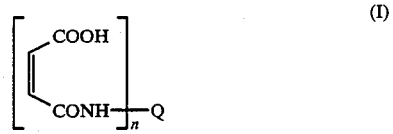
(I)

wherein n and Q are the same as above, with phosgene, in the presence of a catalyst.

Illustrative values for Q are phenyl or phenyl substituted by one or more of alkyl, e.g. methyl, loweralkoxy, e.g. methoxy, halogen, e.g. chloro and/or bromo, acylamido, e.g., acetamido, carboalkoxy, e.g., carboethoxy, acyloxy, e.g., acetoxy, nitro or other noninterfering substituent in the o-, m- and/or p-position.

Examplary compound of formula (I) suitable for use in the process of this invention includes, N-phenylmaleamic acid, N-cyclohexylmaleamic acid, N,N'-(4,4'-diphenylmethane)-bis-maleamic acid, N-p-tolylmaleamic acid, N-3,5-dichlorophenylmaleamic acid, N,N'-(4,4'-diphenylether)-bis-maleamic acid, N,N'-(1,3-phenylene)-bis-maleamic acid, N,N'-(4,4'-diphenylsulfone)-bis-maleamic acid, N,N'-(4,4'-dephenylthioether)-bis-meleamic acid, N,N'-(4,4'-diphenylsulfide)-bis-maleamic acid, N,N'-(3,3'-benzophenone)-bis-maleamic acid, N,N'-[p,p'-(2,2'-diphenylpropane)]-bis-maleamic acid, N,N'-(1,4-naphthylene)-bis-maleamic acid, N-isobutylmaleamic acid, N-(p-dodecylphenyl)-maleamic acid, N-(p-nitrophenyl)-maleamic acid and N-(2,6-dimethylphenyl)-maleamic acid.

These compounds can be prepared according to known processes by reacting maleic anhydride with a monoamine or diamine having the formula:

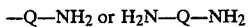

wherein Q has the same values as in the above formula (I). For example, synthesis of N-phenylmaleamic acid can be carried out by dissolving maleic anhydride in an organic solvent such as toluene and followed by adding the amine compound, e.g., aniline, to the resulting solution. An exothermic reaction occurs and crystals of N-phenylmaleamic acid precipitate. The separated crystals can be collected by filtration.

In a preferred embodiment, a compound of formula (I) is produced as described above from maleic anhydride and the selected monoamine or diamine in a reaction solvent suitable for resin the process of this invention and is used therein without isolation as the starting material for the process of this invention.

The amount of phosgene used in the process of this invention can be somewhat more than stoichiomeric, i.e., more than 1 mole per mole of maleamic acid raw material when n is the integer 1 in formula (I), and somewhat more than 2 moles per mole of maleamic acid raw material when n is the integer 2 in formula (I). Usually, up to about a 30% excess over stoichiometric amount is employed.

Phosgenation reaction can be carried out at atmospheric pressure or under increased pressure and can also conducted in the absence of a solvent when the compound of formula (I) is liquid under the reaction conditions.

Generally, the reaction proceeds favorably by using an organic solvent which can dissolve the raw material compounds and is inert in the reaction. Organic solvents suitable for use in the process includes, for example, aliphatic hydrocarbons such as hexane, heptane, n-octane and isooctane; aromatic hydrocarbons such as benzene, xylene, toluene, ethylbenzene and isoprophylbenzene; halogen substituted aromatic hydrocarbons such as chlorobenzene, bromobenzene and dichlorobenzene; aliphatic ethers such as diethyl ether, diisopropyl ether, dioxane and tetrahydrofuran; ketones such as acetone, methyl ethyl kotone, methyl isobutyl ketone and diethyl ketone; and ester such as ethyl acetate, butyl acetate, n-propyl acetate, n-butyl acetate, n-amyl acetate, isoamyl acetate and methyl propionate.

The phosgenation reaction in the process of this invention is carried out in the presence of a reaction catalyst.

Catalysts suitable for us in the reaction include tetraalkylthioureas such as tetramethylthiourea; quaternary ammonium salts such as tetraalkyl ammonium chloride; phosphonium salts such as tetraalkyl phosphonium salts; trisubstituted phosphine oxides such as trimethylphosphine oxide; phosphine sulfides; imidazoles such as imidazole, 2-methylimidazole and N-methylimidazole; and lower aliphatic amides such as dimethylformamide and N-methyl-2-pyrrolidone.

Among these catalyst compounds, imidazoles such as imidazole and lower aliphatic amides such a dimethylformamide and N-methyl-2-pyrrolidone are preferred. The catalytic activity of tetraalkyl ammonium chlorides is somewhat low and an extended reaction time is required when they are employed. Trimethylphosphine oxides have also drawback in high price.

The amount of the catalyst employed is usually from 0.3 to 20 mol % per mole of maleamic acid, preferably from 0.5 to 10 mol % and more preferably from 1 to 5 mol %. An amount less than 0.3 mol % results in a slow reaction rate and a part of the maleamic acid remains unreacted. An amount exceeding 20 mol % is also unfavorable because tarry matter generated as a by-product causes deterioration of the product when a lower aliphatic amide, such as dimethylformamide is used for as the catalyst.

The reaction temperature is usually from 0° to 120° C. and preferably from 20° to 80° C. Reaction temperatures lower than 0° C. are unfavorable because the rate of the reaction is slow and hence a longer period of time is required for completing the reaction.

On the other hand, reaction temperatures in excess of 120° C. are also disadvantageous because side reactions are apt to occur and formation of polymer or tar occurs as a result of insufficient thermal stability of the reaction product at those temperatures.

After completing the reaction, an inert gas, preferably nitrogen gas is desirably blown through the reaction mixture, to conduct degassing of unreacted phosgene. The residual mixture is washed with water to remove phosgene-catalyst complex and dried with a dehydrating agent, such as anhydrous sodium sulfate. Then the solvent is distilled off to obtain the desired product in high yield. The compound thus obtained can be purified by usual purification methods, such as distillation and recrystallization.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees celsius and, unless otherwise indicated, all parts and percentages are by weight.

The entire texts of all application, patents and publications, if any, cited herein are incorporated by reference.

The present invention will hereinafter be illustrated further in detail by way of examples.

EXAMPLE 1

To a 1 liter round bottom flask equipped with a stirrer, condenser, thermometer and a gas inlet tube, 69.3 g (0.71 mole) of maleic anhydride and 520 g of toluene were charged to form a solution. To this solution, 65.2 g (0.70 mole) of aniline was added over an hour at 10°-50° C.

After stirring the reaction mixture for an additional hour at the same temperature, 1.5 g (0.021 mole) of dimethyl formamide was added and then 76.7 g (0.77 mole) of phosgene was blown into the mixture at 45°-50° C. over 4 hours to carry out ring closing and addition reactions. Thereafter nitrogen gas was blown through the reaction mixture to conduct phosgene degassing. Then 50 ml of water was added and stirred to wash the reaction mixture, followed by removing the separated water layer. The procedure was repeated twice to remove a phosgene complex of dimethylformamide. The washed reaction mixture was dried over anhydrous sodium sulfate and toluene solvent was distilled off under reduced pressure. N-Phenylmonochlorosuccinimide thus obtained was 151.6 g (97.0% of theoretical yield) and had a melting point of 117°-118° C.

EXAMPLE 2

Using the same apparatus as described in Example 1, 34.7 g (0.354 mole) of maleic anhydride was dissolved in 260 g of toluene and 34.7 g (0.350 mole) of cyclohexylamine was added to the resulting solution over 0.5 hour at 10°-50° C. After stirring the reaction mixture for 0.5 hour at the same temperature, 1.27 g (0.0175 mole) of dimethylforamide was added and 38.1 g (0.385 mole) of phosgene was then blown into the reaction mixture over 4 hours at 35°-40° C. After raising the temperature to 70°-75° C., nitrogen gas was blown through the reaction mixture for 2 hours to carry out phosgene degassing and water was added to wash the reaction mixture. The reaction mixture was dried. Solvent was removed and the residue was vacuum distilled at 138°-140° C., 1-2 mmHg. The N-Cyclohexylmonochlorosuccinimide thus obtained (72.7 g, 96.6% of theoretical yield) had a melting point of 63°–64° C.

EXAMPLE 3

Using the same apparatus as described in Example 1, 29.7 g (0.303 mole) of maleic anhydride was dissolved in 180 ml of ethyl acetate. A solution of 29.7 g (0.15 mole) of bis(4-aminophenyl)methane in 120 ml of ethyl acetate was added to the above solution over 0.5 hours at 10°–50° C.

After stirring the mixture for 0.5 hours at the same temperature, 2.376 g (0.032 mole) of dimethylformamide was added and 38.1 g (0.385 mole) of phosgene was blown into the reaction mixture over 4 hours at 45°–50° C. to carry out ring closing and addition reactions. Thereafter nitrogen gas was blown through the reaction mixture to conduct degassing and water was then added to wash the reaction mixture. The resultant reaction mixture was dried, concentrated and crystallized.

The N,N'-(4,4'-diphenylmethane)-bis-monochlorosuccinimide thus obtained (63.0 g, 97.4% of theoretical yield) had a melting point of 159°–165° C. (decomp.)

EXAMPLE 4

The same procedures as described in Example 1 were carried out except that 86.1 g (0.7 mole) of 4-methoxyaniline was used in place of 65.2 g (0.7 mole) of aniline and the reaction was carried out at 50°–60° C. for 5 hours. The N-p-Methoxyphenylchlorosuccinimide thus obtained (164.4 g, 96% of theoretical yield) had a melting point of 142°–143° C.

EXAMPLE 5

The same procedures as described in Example 1 were carried out except that 37.4 g (0.35 mole) of m-toluidine was used in place of 65.2 g (0.70 mole) of aniline, 1.5 g (0.021 mole) of imidazole was used in place of 1.27 g (0.0175 mole) of dimethylformamide, and the reaction was conducted at 60°–70° C. for 5 hours. The N-m-Tolylchlorosuccinimide thus obtained (76.9 g, 96.3% of theoretical yield) had a melting point of 137°–138° C.

EXAMPLE 6

The same procedures as described in Example 1 were carried out except that 96.6 g (0.7 mole) of m-nitroaniline was used in place of 65.2 g (0.7 mole) of aniline, 1.43 g (0.021 mole) of imidazole was used in place of 1.5 g (0.021 mole) of dimethylformamide, and butyl acetate was used as the reaction solvent. The N-m-Nitrophenylchlorosuccinimide thus obtained (175.5 g, 96.5% of theoretical yield) had a melting paint of 145°–146° C.

COMPARATIVE EXAMPLE

To a 500 ml round bottom flask equipped with a stirrer, condenser, thermometer and a dropping funnel, 34.6 g (0.35 mole) of maleic anhydride and 250 g of toluene were charged to make a solution. To this solution, 32.6 g (0.35 mole) of aniline was added dropwise over an hour at 10°–30° C.

After stirring the mixture for 30 minutes at the same temperature, 41.6 g (0.35 mole) of thionyl chloride was added dropwise to the reaction mixture at 20°–30° C. The temperature of the reaction mixture was gradually raised and stirring was continued at 50°–70° C. until evolution of hydrogen chloride gas and sulfur dioxide was stopped.

The resulting solution was washed with a dilute aqueous solution of sodium carbonate, dried over anhydrous sodium sulfate and and the solvent was distilled off under reduced pressure. The yellow crystals of N-phenylmonochlorosuccinimide thus obtained (121.9 g, 79% of theoretical yield) had a melting point of 115°–117° C.

What is claimed is:

1. A process for the preparation of an N-substituted monochlorosuccinimide of the formula:

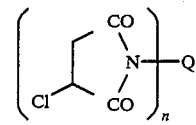

wherein n is an integer of 1 or 2 and, when n is 1, Q is phenyl or phenyl substituted one or more alkyl, alkoxy, acetoamido, carboalkoxy, acyloxy, nitro in the o-, m- and/or p-position, an alkyl group or a cycloalkyl group and, when n is 2, Q is a divalent organic group of an unsubstituted phenyl group, unsubstituted naphthylene group, or biphenyl group of the formula

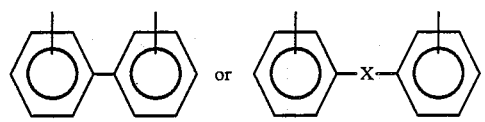

wherein X is a divalent bridging group of

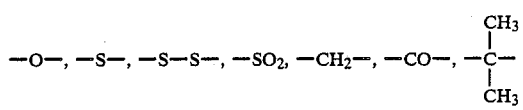

which comprises reacting a corresponding maleamic acid represented by the formula:

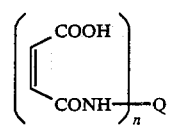

wherein n and Q have the values given above, with phosgene, in the presence of a catalyst.

2. The process as claimed in claim 1 wherein n is 1.

3. The process as claimed in claim 1 wherein n is 2.

4. The process as claimed in claim 2 wherein the maleamic acid is N-phenylmaleamic acid or N-cyclohexylmaleamic acid.

5. The process as claimed in claim 3 wherein the maleamic acid is N,N'-(4,4'-diphenylmethane)-bis-maleamic acid.

6. The process as claimed in claim 1 wherein the catalyst is an imidazole or a lower aliphatic amide.

7. The process as claimed in claim 6 wherein the catalyst is imidazole.

8. The process as claimed in claim 6 wherein the catalyst is dimethylforamide or N-methyl-2-pyrrolidone.

9. The process as claimed in claim 1 wherein the amount of the catalyst used is from 0.3 to 20 mol % per mole of the maleamic acid.

10. The process as claimed in claim 1 wherein the reaction is conducted at a temperature is from 20° to 80° C.

11. The process as claimed in claim 1 wherein the reaction is carried out in aromatic hydrocarbon.

12. The process as claimed in claim 7 wherein the aromatic hydrocarbon is toluene.

13. The process as claimed in claim 1 wherein the reaction carried out in a volatile ester as an inert organic.

14. The process as claimed in claim 13 wherein the ester is ethyl acetate.

15. The process as claimed in claim 1 wherein the maleamic acid is N-phenylmaleamic acid or N-cyclohexylmaleamic acid, wherein the reaction is carried out from 20° to 80° C. in an aromatic hydrocarbon or a volatile ester as an inert inorganic solvent and wherein the catalyst is dimethylformamide, imidazole or pyrrolidone from 0.3 to 20 mol % per mole of the maleamic acid.

16. The process of claimed 1 wherein the starting maleamic acid is produced by reacting maleic anhydride with a monoamine or diamine of the formula Q—NH$_2$ or H$_2$N—Q—NH$_2$ wherein Q has the values given therein.

17. The process of claimed 16 wherein the starting maleamic acid is produced in a reaction solvent suitable for use in the production of the corresponding N-substituted monochlorosuccinimide and is used without isolation therefrom.

* * * * *